United States Patent
Shibuya et al.

(10) Patent No.: US 7,842,237 B1
(45) Date of Patent: Nov. 30, 2010

(54) AUTOMATIC ANALYZER AND RACK TRANSFER DEVICE

(75) Inventors: Takeshi Shibuya, Hitachinaka (JP);
Hiroyasu Uchida, Hitachinaka (JP);
Katsuhiro Kanbara, Hitachinaka (JP)

(73) Assignee: Hitachi, Ltd., Tokyo (JP)

( * ) Notice: Subject to any disclaimer, the term of this patent is extended or adjusted under 35 U.S.C. 154(b) by 0 days.

(21) Appl. No.: 10/069,578

(22) PCT Filed: Jan. 12, 2000

(86) PCT No.: PCT/JP00/00100
§ 371 (c)(1),
(2), (4) Date: Feb. 27, 2002

(87) PCT Pub. No.: WO01/51929
PCT Pub. Date: Jul. 19, 2001

(51) Int. Cl.
*G01N 21/00* (2006.01)
(52) U.S. Cl. ............... 422/64; 422/63; 422/65; 422/67; 422/99; 422/100; 436/180
(58) Field of Classification Search ............. 422/63–65, 422/99–101, 67; 436/180
See application file for complete search history.

(56) References Cited

U.S. PATENT DOCUMENTS

| | | | |
|---|---|---|---|
| 4,719,087 A * | 1/1988 | Hanaway | 422/102 |
| 5,833,925 A | 11/1998 | Shu et al. | |
| 6,080,364 A * | 6/2000 | Mimura et al. | 422/67 |
| 6,290,907 B1 * | 9/2001 | Takahashi et al. | 422/65 |
| 6,409,968 B1 * | 6/2002 | Takahashi | 422/64 |
| 2004/0057872 A1 * | 3/2004 | Shibuya et al. | 422/64 |

FOREIGN PATENT DOCUMENTS

| | | |
|---|---|---|
| EP | 0325101 | 7/1989 |
| EP | 0856736 A2 | 8/1998 |
| EP | 0871034 A2 | 10/1998 |
| JP | 63-52061 | 3/1988 |
| JP | 1-212362 | 8/1989 |
| JP | 1-250759 | 10/1989 |
| JP | 02066461 * | 3/1990 |
| JP | 5-72215 | 3/1993 |
| JP | 6-148202 | 5/1994 |
| JP | 8-35970 | 2/1996 |
| JP | 8-510554 | 11/1996 |
| JP | 943249 | 2/1997 |
| JP | 10-339732 | 12/1998 |

* cited by examiner

*Primary Examiner*—Jyoti Nagpaul
(74) *Attorney, Agent, or Firm*—Mattingly & Malur, P.C.

(57) ABSTRACT

An automatic analyzer which is applied to a device for analyzing specimen by the transfer of a specimen holding rack to an analysis unit and designed not to complicate the transfer system of the rack even if the number of the analysis units is one or increased to two or more, wherein a rack standby disk capable of rotating and stopping under the condition that a plurality of racks are waiting is installed, an exclusive rack reciprocatingly transfer line is provided between each analysis unit and the rack standby disk, only a single rack is led to each rack reciprocatingly transfer line, and the rack is returned to the rack standby disk after the sampling and treatment of the specimen have been completed.

10 Claims, 7 Drawing Sheets

FIG. 5

| RACK ROTATING TABLE | | ANALYSIS-SIDE CONNECTION LINE | |
|---|---|---|---|
| RACK POSITION No. | STATE OF USE | ANALYSIS UNIT | STATE OF USE |
| 1 | 0 | 1 | 1 |
| 2 | 0 | 2 | 0 |
| 3 | 0 | SUBTOTAL | 1 |
| 4 | 1 | | |
| 5 | 1 | | |
| 6 | 1 | | |
| 7 | 0 | | |
| 8 | 1 | | |
| 9 | 1 | | |
| 10 | 0 | | |
| 11 | 1 | | |
| 12 | 0 | | |
| 13 | 0 | | |
| 14 | 1 | | |
| 15 | 1 | | |
| SUBTOTAL | 8 | | |
| TOTAL | 9 | | |

US 7,842,237 B1

AUTOMATIC ANALYZER AND RACK TRANSFER DEVICE

BACKGROUND OF THE INVENTION

1. Technical Field

The invention relates to an automatic analyzer, in which racks holding specimens being analyzed are transferred and the specimens are sampled by analysis units, and a method of transferring racks.

2. Background Art

Results of analysis of vital specimens such as plasma, serum, urine or the like give rise to much information in diagnosis of the condition of a disease. JP-A-10-339732 describes an apparatus for automatically analyzing such vital specimens. With this prior art, a plurality of analysis units are arranged along a transfer line comprised of a belt conveyor, a rack supply section being arranged on one end side of the transfer line and a rack recovery section being arranged on the other end side. A rack holding a specimen stops at one or more analysis units and then is recovered by the rack recovery section.

Further, the JP-A-10-339732 discloses a constitution, in which in addition to the rack supply section for common specimens, a supply section is provided to repeatedly supply standard liquid racks and control specimen racks, these two supply sections being connected to the transfer line.

Also, Japanese National Publication No. 8-510554 discloses a constitution, in which a loading device for loading sample carriers onto a loop-shaped conveyor, an unloading device for unloading from the conveyor and a plurality of analysis modules are arranged around the conveyor, and a turntable is arranged between the loop-shaped conveyor and the respective analysis modules to be able to rotate the plurality of sample carriers.

DISCLOSURE OF THE INVENTION

Like the automatic analyzer described in the above-mentioned JP-A-10-339732 and Japanese National Publication No. 8-510554, in the case where a multiplicity of racks are transferred by a lengthy conveyor used in common for transferring racks to a plurality of analysis units, advancing of racks is impeded even when an obstacle is generated at one location on the transfer conveyor, so that the rack transfer operation in the entire apparatus cannot be continued.

Also, with the above-mentioned prior art, in the case where an automatic analyzer is of a minimum unit provided with only one analysis unit, it becomes too large in size as a whole, which requires modification of a common transfer conveyor when two or more analysis units are to be additionally installed.

An object of the invention is to provide an automatic analyzer which can be small-sized even when it is comprised of a minimum unit provided with one analysis unit, and obviates modification of an existing transfer system when additional analysis units are to be installed, and a rack transfer method.

In the invention, racks from a rack supply section are received by a rack standby disk capable of rotating and stopping in a state, in which a plurality of racks holding specimens are made to stand by, a rack reciprocating transfer means provided to correspond to an analysis unit or units, which implement analysis and treatment of a specimen or specimens is used to transfer a single rack toward a specimen sampling position on the analysis unit from the rack standby disk, a single aftertreatment rack, from which a specimen for analysis and treatment is sampled in the specimen sampling position on the analysis unit, is returned to the rack standby disk by the rack reciprocating transfer means, and the aftertreatment rack on the rack standby disk is carried out toward a rack recovery section.

BRIEF DESCRIPTION OF THE SEVERAL VIEWS OF THE DRAWING

FIG. 5 is a view illustrating a management table.

DETAILED DESCRIPTION OF THE INVENTION

An embodiment of the invention will be explained with reference to FIGS. 1 to 6. An automatic analyzer in this embodiment is designed to analyze specimens of plasma, serum or urine. The automatic analyzer shown in FIG. 1 comprises an example of minimum unit, in which one rack delivery unit 1 and one analysis unit 2 are combined with each other but may be designed such that two or more analysis units are combined with one rack delivery unit. A single analysis unit can analyze and treat a plurality of analysis items with respect to respective specimens being analyzed.

Figure 1:
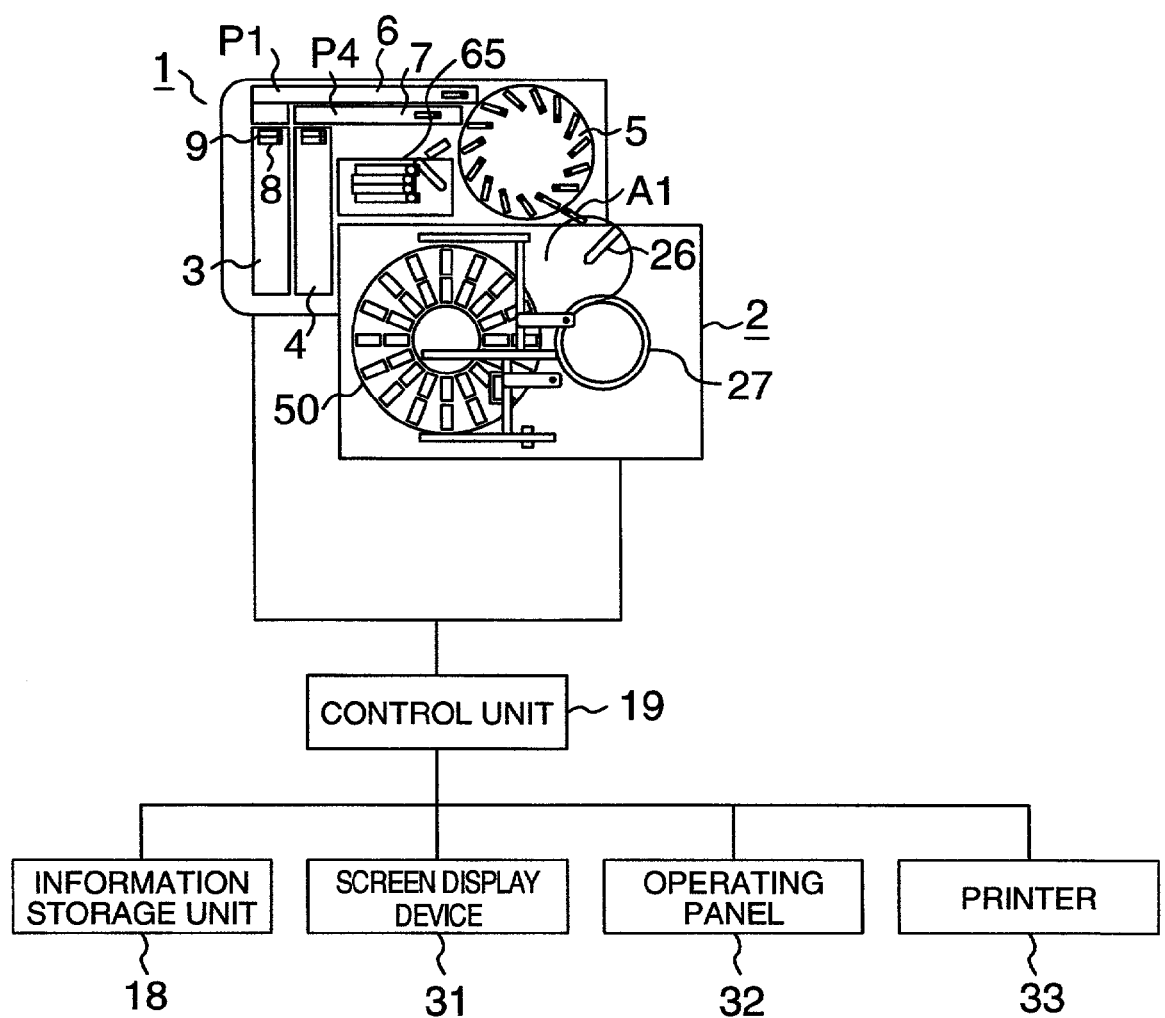
FIG. 1 is a plan view showing the schematic construction of an automatic analyzer as an embodiment, to which the invention is applied.
Figure 2:
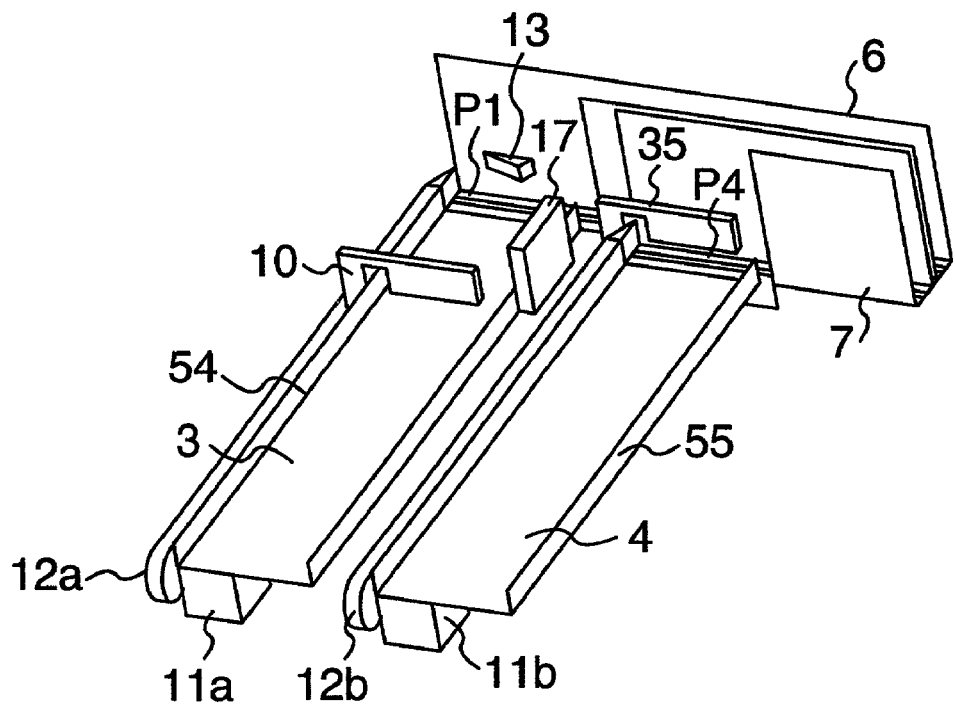
FIG. 2 is a perspective view showing a rack supply section, a rack recovery section and a neighbor thereof in the automatic analyzer shown in FIG. 1.
Figure 3:
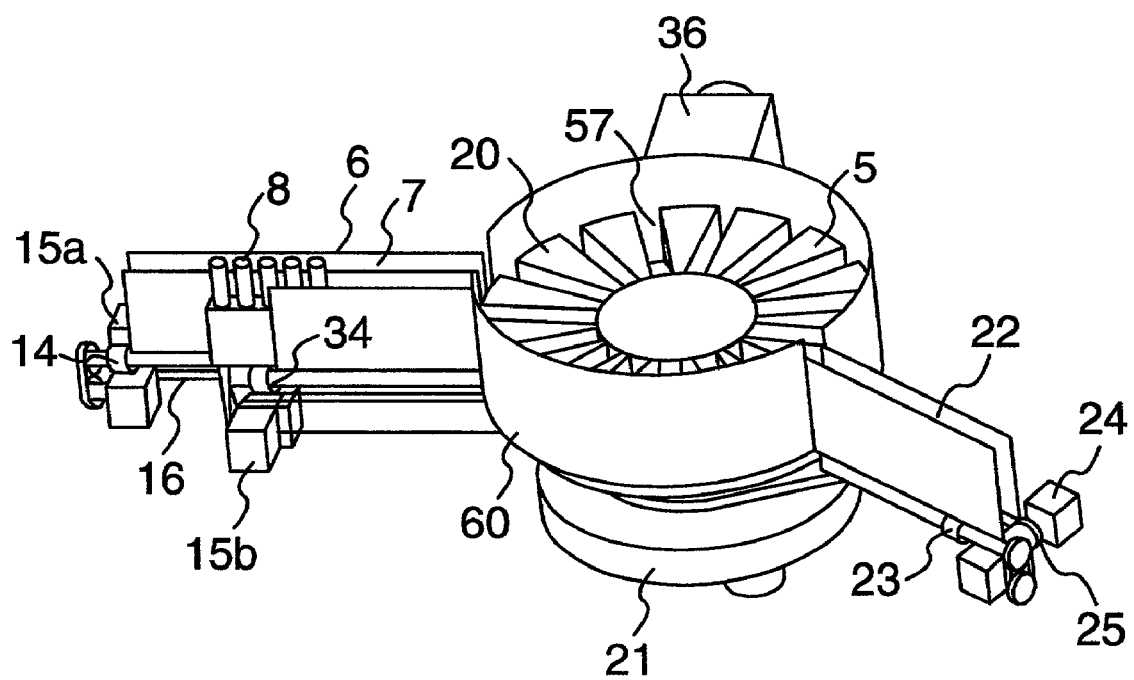
FIG. 3 is a perspective view illustrating a schematic construction near a rack standby disk in the automatic analyzer shown in FIG. 1.
Figure 4:
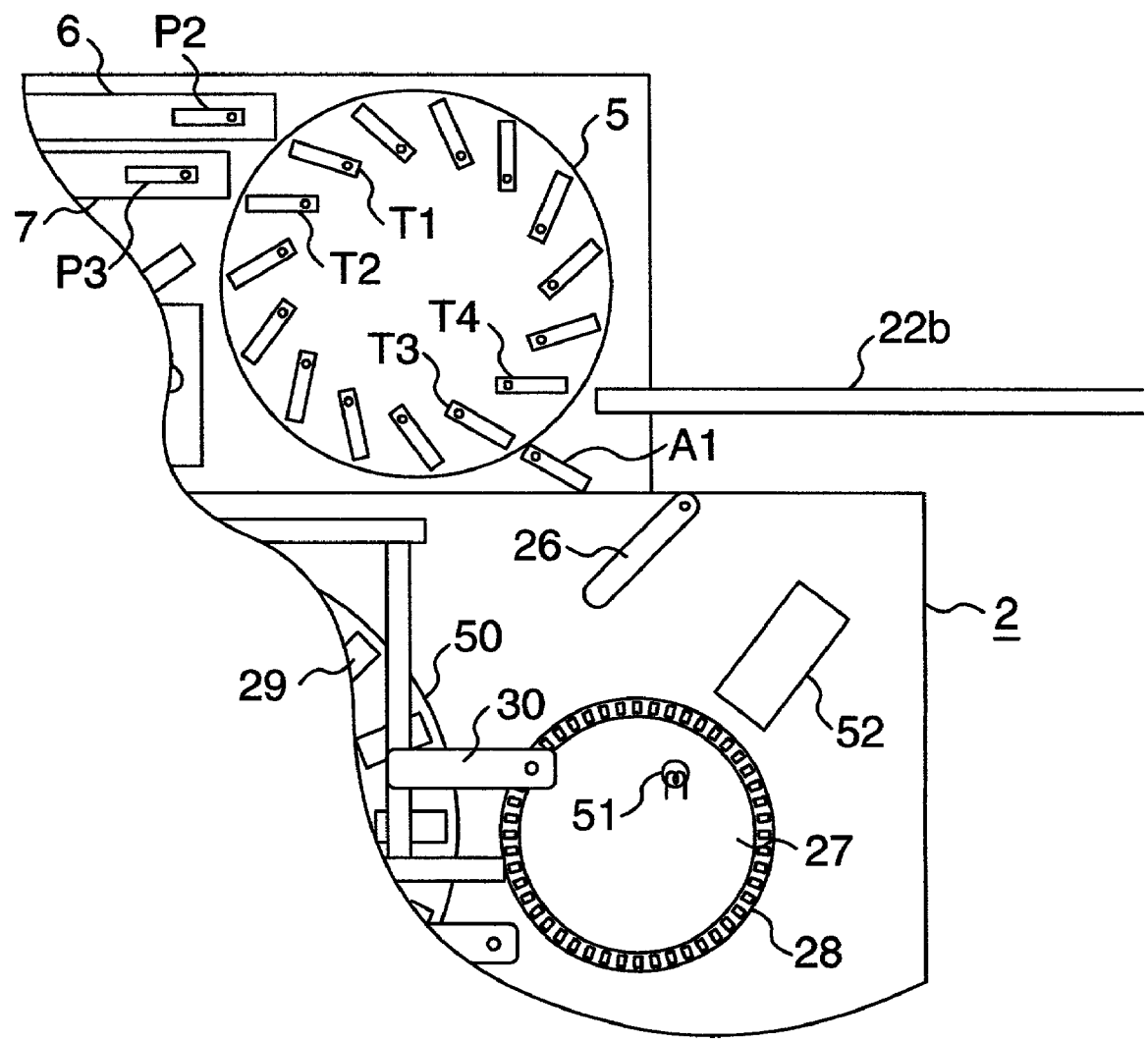
FIG. 4 is a fragmentary plan view illustrating the relationship between the rack standby disk and a sampling mechanism of an analysis unit.
Figure 6:
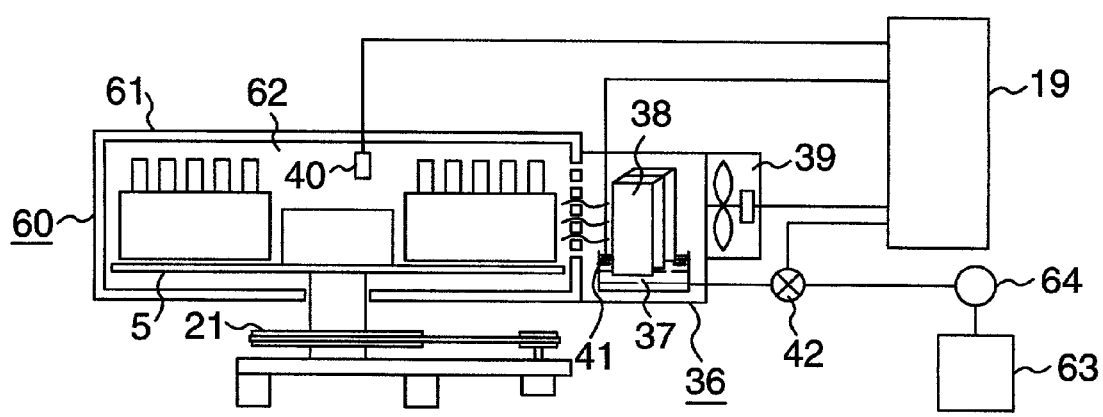
FIG. 6 is a schematic, cross sectional view illustrating a part near an evaporation protecting chamber in the automatic analyzer shown in FIG. 1.

FIG. 2 is a perspective view showing a rack supply section 3, a rack recovery section 4 and a neighbor thereof in the automatic analyzer shown in FIG. 1. FIG. 3 is a perspective view showing a rack standby disk 5 and a neighbor thereof in the automatic analyzer shown in FIG. 1. FIG. 4 is a fragmentary plan view illustrating the relationship between the rack standby disk 5 and a sampling mechanism 26 of the analysis unit 2 in the automatic analyzer shown in FIG. 1. FIG. 5 is a view showing a management table in an information storage unit 18. FIG. 6 is a schematic, cross sectional view illustrating the relationship between an evaporation protecting chamber and the rack standby disk in the automatic analyzer shown in FIG. 1.

The rack delivery unit 1 comprises the rack supply section 3 capable of transferring pretreatment racks, which holds specimens prior to sampling, toward the rack standby disk 5, the rack recovery section 4 for recovering aftertreatment racks for which the sampling and treatment of the specimen have been completed by the sampling mechanism 26 of the analysis unit 2, the rack standby disk 5 capable of operatively rotating a plurality of racks while holding them and stopping so as to position a desired rack in a desired location, a rack feed line 6 for conducting the pretreatment racks toward the rack standby disk 5 from the rack supply section 3, and a rack recovery line 7 for conducting the aftertreatment racks toward the rack recovery section 4 from the rack standby disk.

The rack 9 is a substantially rectangular-shaped box body and preferably comprises a plurality of reception chambers, into which a plurality of specimen containers can be charged. A discriminating information medium indicative of discriminating information of a stored liquid is provided on an outer wall of a common specimen container, which contains therein a common specimen such as a patient specimen, a calibrator container containing therein a calibrator liquid (standard liquid) for formation of a working curve, a quality control container containing therein a control specimen, which is one for quality control, a cleaning liquid container containing therein a cleaning liquid, which includes a special cleaning agent, and the like. The discriminating information as a specimen information in a specimen container includes a receipt number, receipt date, patient's name, patient number, kind of specimen, items of requested analysis, and so on. A discriminating information medium indicative of rack discriminating information is provided on a common rack container for patient specimen, into which various containers are charged, a calibrator rack, a rack for quality control, a cleaning liquid rack and the like. The discriminating information includes a stored liquid name, rack number, manufacture lot number and so on. Bar code labels, magnetic recording medium and the like are used as the discriminating information medium.

The rack supply section 3 and the rack recovery section 4, respectively, have a push lever 10, for moving the pretreatment racks one pitch by one pitch as shown in FIG. 2. For racks transferred to the rack feed line 6, the rack discriminating information and/or the container discriminating information (specimen discriminating information) of a container on an associated rack is read by a bar-code reading device 17 to be transferred to a control unit 19. In the rack supply section 3, the push lever 10 pushes a rear surface of a rearmost rack among the row of racks on a tray 54 defining an area where a multiplicity of racks are aligned, to move the row of racks, so that when a forefront rack is pushed to an inlet position P1 of the rack feed line 6 to come into contact with a rack sensor 13 provided on an end wall, a signal thus produced is transmitted to the control unit 19 to cause stopping of an action of the push lever 10. The push lever 10 is mounted to a revolving belt 12a which in turn is driven by a motor 11a.

When the aftertreatment racks transferred on the rack recovery line 7 reaches an outlet position P4 of the line, the push lever 35 standing by at a rear surface of the outlet P4 makes a rack pushing action. The rack recovery section 4 is provided with a tray 55 having an area for receiving a multiplicity of aftertreatment racks. The push lever 35 is mounted to a revolving belt 12b which in turn is driven by a motor 11b. When several racks have been already present on the tray 55, the push lever 35 pushes a row of racks one pitch by one pitch from rearward.

Movements of racks between the rack delivery unit 1 and the analysis unit 2 are implemented via an analysis-side connection line 22 shown in FIG. 3. The analysis-side connection line 22 is used exclusively for a single analysis unit, and operatively controlled by the control unit 19 so as to receive only one rack. Defined near a tip end of the analysis-side connection line 22 is a specimen sampling position A1 of the analysis unit 2 such that a single rack reciprocates between the rack standby disk 5 and the specimen sampling position A1.

The rack standby disk 5 is operatively controlled by the control unit 19 so as to enable holding the pretreatment racks, aftertreatment racks, control racks, calibrator racks, cleaning liquid racks, second measurement waiting racks and the like in a mingled state. As shown in FIG. 3, the rack standby disk 5 comprises a plurality of rack receipt sections 57 partitioned by partition members 20, rotating action of the respective rack receipt sections 57 being controlled by the control unit 19 so as to be able to stop in a pretreatment rack receipt position where pretreatment racks are to be received from the side of rack supply section 3, an aftertreatment rack carrying-out position where aftertreatment racks held there are to be carried out toward the rack recovery section, an access position for analysis where pretreatment racks are to be carried out toward the analysis unit 2, and a position where racks are to be taken in and out to a specimen sampling position of a measurement section 65 for items of electrolyte analysis. The access position for analysis serves also as a position where racks are received from the specimen sampling position A1. A drive mechanism 21 for positioning of the rack standby disk 5 is provided with a position sensor.

The rack standby disk 5 is disposed within an evaporation protecting chamber 60 to be rotatable. Air within the evaporation protecting chamber 60 is made by means of a humidifier 36 described later higher in humidity than an outside air. In this case, humidity is kept at, for example, 80% or higher. As seen from FIGS. 2, 3 and 4, pretreatment racks present on the rack feed line 6 are moved toward the rack receipt sections 57 on the rack standby disk 5 by means of a rack moving pawl 14 mounted on the belt 16 driven by the motor 15a. Also, aftertreatment racks present on the rack recovery line 7 are moved toward the outlet position P4 from the rack standby disk 5 by means of a rack moving pawl 34 mounted on the belt driven by the motor 15b. With an example shown in FIG. 3, fifteen racks can be held on the rack standby disk 5. A side of the rack standby disk 5, the partition members 20, a bottom plate of the disk and the like are formed to allow racks and the rack moving pawls to come in and go out. The rack standby disk is driven by the drive mechanism 21 to be rotatable in forward and rearward directions.

Connected to the evaporation protecting chamber 60 is the analysis-side connection line 22 as well as the rack feed line 6 and the rack recovery line 7. Movements of racks between the access position T3 for analysis on the rack standby disk 5 and the specimen sampling position A1 on the analysis-side connection line 22 are implemented by a rack moving pawl 23 mounted on a belt 25 driven by a motor 24. These moving operations are controlled by the control unit 19.

As shown in FIGS. 1 and 4, the analysis unit 2 comprises a reaction disk 27 for repeatedly rotating a row of reaction containers 28, which are arranged in a circular configuration, a predetermined angle in a predetermined direction and stopping them. The reaction disk may rotate in forward and rearward directions. Also, the analysis unit 2 comprises a reagent disk 50 carrying thereon a plurality of reagent containers 29, in which reagents for a plurality of analysis items are received, a reagent dispensing mechanism 30 for dispensing reagents conformed to the analysis items to the reaction containers 28 from the reagent containers 29, and the specimen sampling mechanism 26, which uses a pipette nozzle to dispense specimens conformed to the analysis items to the reaction containers 28 from a specimen container 8 held by that rack which has reached to the specimen sampling position A1. Reaction liquids generated by mixing of specimens and reagents in the reaction containers 28 are measured by a multi-wave photometer 52, which receives light transmitted through the reaction containers 28 by a light source 51, and measurement data is treated by the control unit 19, the result of analysis being indicated on a printer 33 and a screen display device 31.

When the specimen containers 8 containing therein specimens such as patient specimens are received by a receipt installation, these specimen containers are charged in the racks 9 and specimen information and analysis information are input by an operator into the control unit 19 from an operating panel 32. The specimen information includes at least specimen numbers and information of items to be analyzed every specimen. Charged into the rack supply section 3 are particular racks, such as racks for quality control (control racks), calibrator racks, cleaning racks and the like, forwardly of racks for common specimens. Prior to the beginning of the analyzing operation of the automatic analyzer shown in FIG. 1, these particular racks are transferred to the rack standby disk 5. In the course of transfer effected by the rack feed line 6, discriminating information of containers and/or racks is read by the bar-code reading device 17 to be transmitted to the control unit 19. The control unit 19 judges and stores, on the basis of the thus read information, kinds of liquids held on the particular racks to make them profit for subsequent transfer control of particular racks.

When the analyzing operation by the automatic analyzer is started, a plurality of common racks as a whole set at the rack supply section 3 are moved toward the rack feed line 6 by the push lever 10, and when a forefront rack is sensed by the rack sensor 13, movements are stopped. A direction, in which the racks 9 are moved on the rack feed line 6, is substantially perpendicular to a direction, in which they are moved in the rack supply section 3, and a direction, in which the racks are moved on the rack recovery line 7, is substantially perpendicular to a direction, in which they are moved in the rack recovery section 4. For the racks 9 transferred on the rack feed line 6, the specimen discriminating information or the rack discriminating information is read by the bar-code reading device 17 to be transferred to the control unit 19. The control unit 19 compares the thus read information with information regarding respective specimens, being analyzed, beforehand input from the operating panel 32 and stored in the information storage unit 18, and controls the analysis unit 2 in a manner to have the same performing an analyzing operation conformed to the analysis items for respective specimens.

While racks having been moved along the rack feed line 6 by the rack moving pawl 14 are transferred to an outlet position P2 of the rack feed line 6, the control unit 19 searches and stores, on the basis of the stored information, an empty rack receipt section 57 in the rack standby disk 5 to operatively rotate the rack standby disk 5 in a manner to position the empty rack receipt section 57 to a carrying-in position T1. A pretreatment rack in the outlet position P2 is carried by the rack moving pawl 14 into the empty rack receipt section 57 positioned in the carrying-in position T1 facing the outlet position P2.

The plurality of rack receipt sections 57 formed on the rack standby disk 5 are disposed so that a direction, in which a rack enters, intersects a normal direction and also intersects a direction perpendicular to the normal direction (see FIG. 4). With such arrangement and configuration of the rack receipt sections, even the disk of small diameter can receive many racks. The rack moving pawl 14 having completed transferring the pretreatment racks to the rack standby disk 5 is returned to a standby position at an end on the side of the inlet position P1 of the rack feed line 6 to be ready for transferring of subsequent fresh racks. When aftertreatment racks, of which treatment has been completed and which are waiting for recovery, are present on the rack standby disk 5, they are positioned at a carrying-out position T2 facing an inlet position P3 of the rack recovery line 7, and thus standing-by racks are carried out by the rack moving pawl 34 to the rack recovery line 7 from the rack standby disk 5.

Pretreatment racks received by the rack standby disk 5 are moved to the access position T3 for analysis by virtue of rotation of the rack standby disk 5. A single pretreatment rack stopped at the access position T3 for analysis is pulled out of the rack standby disk 5 by the rack moving pawl 23, and further moved along the analysis-side connection line 22 to be conducted to the specimen sampling position A1 on the analysis-side connection line 22. Thereby, since an entire length of the single pretreatment rack is disposed in a distant position where rotation of the rack standby disk 5 is not impeded, the rack standby disk 5 can perform its rotating operation for transfer of other racks while the single pretreatment rack is subjected to the sampling and treatment of the specimen in the specimen sampling position A1.

In the specimen sampling position A1 of the analysis unit 2, sampling of specimens is implemented by the specimen sampling mechanism 26 having a pipette nozzle, which can be moved vertically and horizontally by a turning arm. A predetermined amount of a specimen received in a forefront one among the specimen containers 8 held in the rack 9 is first drawn into the pipette nozzle conformed to the analysis items, the drawn specimen being discharged into the reaction container 28 on the reaction disk 27. When there are a plurality of analysis items for the same specimen, the specimen in the same specimen container is likewise drawn into and discharged from different reaction containers. After sampling of a specimen is completed with respect to a forefront specimen container, the rack 9 is moved one position by the rack moving pawl 23, and sampling operation of a specimen is likewise implemented for a second specimen container. Subsequently, sampling operation of a specimen successively implemented by the specimen sampling mechanism 26 and when sampling operation of a specimen is complemented with respect to a last specimen container, the single rack is transferred by the rack moving pawl 23 to be returned to the rack standby disk via the analysis-side connection line 22. Before the rack reaches the rack standby disk 5, the control unit 19 controls rotating motion of the rack standby disk in a manner to position an empty rack receipt sections 57 in the access position T3 for analysis.

A rack having been charged into the empty rack receipt sections 57 by virtue of the action of the rack moving pawl 23 to be subjected a first sampling of a specimen is made to stand by on the rack standby disk 5 until results of analysis for a sampled specimen in terms of respective analysis items are obtained in the analysis unit 2. In case of a specimen for which the results of analysis are unfavorable and which needs further analytical measurements, an associated rack is again positioned in the access position T3 for analysis to be transferred to a specimen sampling position in the analysis unit 2 where sampling of a specimen is implemented for a required specimen which is again subjected to analytical measurements, and the rack, for which the sampling operation is terminated, is returned to the rack standby disk.

In the case where there are obtained results of analysis indicative of no need for further measurements of a rack, for which a first sampling of a specimen is terminated, the rack is positioned in the carrying-out position T2 to be carried out toward the rack recovery section 4 by the rack moving pawl 34. A rack, for which a further sampling of a specimen is terminated, is likewise carried out toward the rack recovery section 4. The rack moving pawl 34 transfers aftertreatment racks to the outlet position P4 of the rack recovery line 7 from the carrying-out position T2. A rack in the outlet position P4 is pushed onto the tray 55 on the rack recovery section 4 by the push lever 35 to be recovered there.

Meanwhile, the reagent dispensing mechanism 30 causes a predetermined amount of a reagent conformed to an analysis item to be added to the reaction containers 28 having received specimens every analysis item from the specimen sampling mechanism 26, thus reaction of a mixed liquid of the specimen and the reagent being started. The reaction liquid in the reaction containers 28 is measured at a wavelength suited for measurements of a reaction product by the multi-wave photometer 52, whereby concentration in a specimen being an analysis item is calculated on the basis of absorption property, fluorescent property, luminous property and so on, and the calculated results of analysis are output to the screen display device (for example, CRT) 31 and/or a printer 33.

Figure 7:
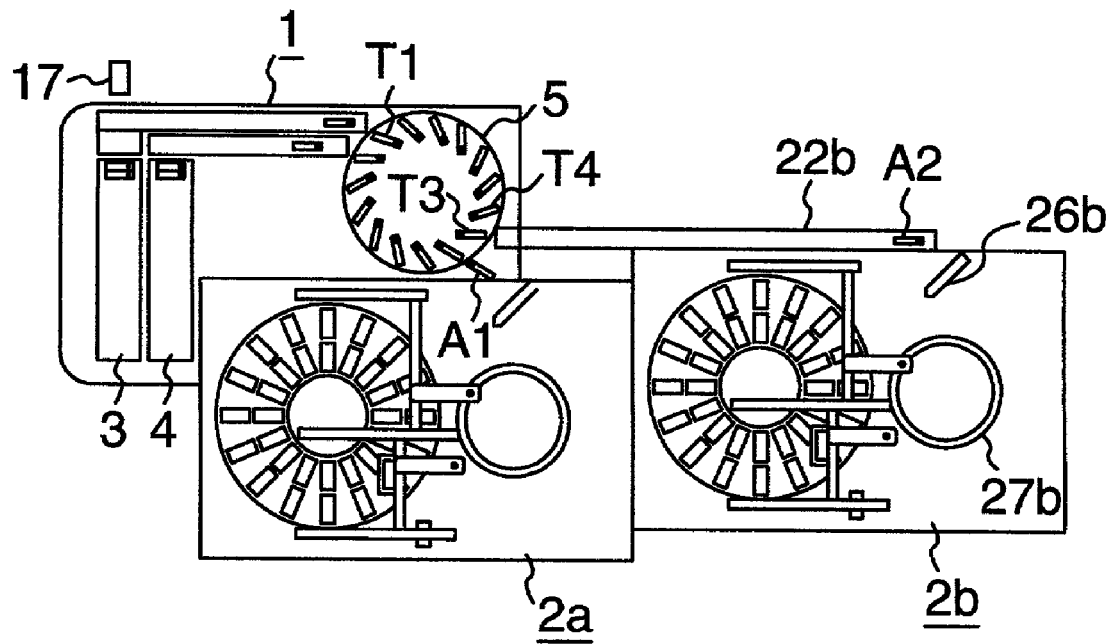
FIG. 7 is a schematic, plan view showing an example of an arrangement, in which two analysis units are combined.
Figure 8:
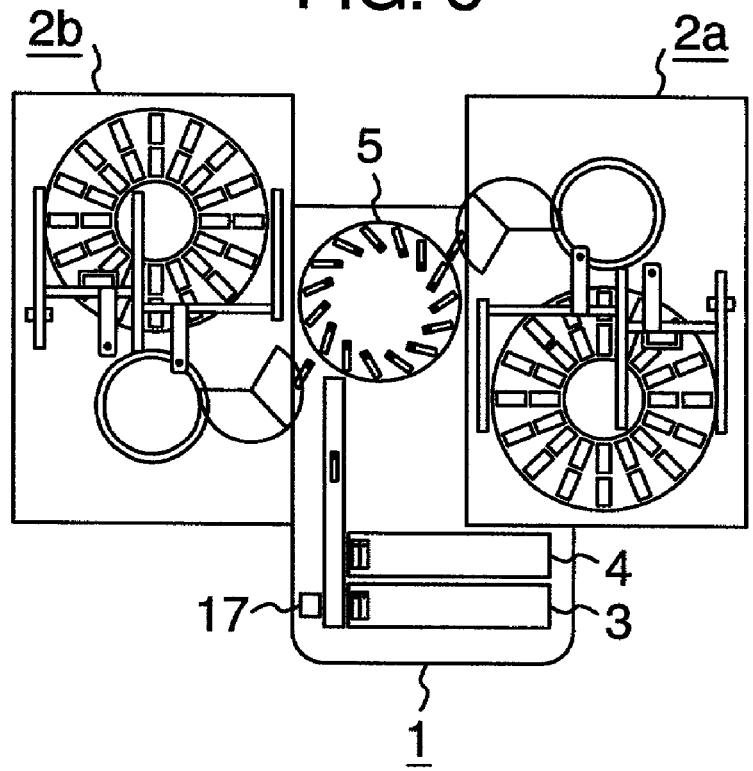
FIG. 8 is a schematic, plan view showing another example of an arrangement, in which two analysis units are combined.

With the use of a rack management table, which is formed on the basis of information every rack stored in the information storage unit 18, the control unit 19 controls and manages transfer of respective racks. Hereupon, an explanation will be given to the rack management table with reference to FIG. 5. In the table shown in FIG. 5, it is assumed that the rack standby disk 5 is connected to two analysis units as shown in FIG. 7 or 8, which will be described later, via respective exclusive analysis-side connection lines 23.

Presence and non-presence of racks in the respective rack receipt sections (rack positions) 57 on the rack standby disk 5 are set by the control unit 19 to be 1 or 0 on the rack management table. Presence and non-presence of racks on the analysis-side connection lines for exclusive use in the respective analysis units are also set by the control unit to be 1 or 0 on the rack management table. 1 indicates presence of a rack or racks and 0 indicates non-presence of a rack. While the number of the rack receipt sections on the rack standby disk 5 is assumed to be fifteen, eight racks are present on the rack standby disk 5 in the example shown in FIG. 5 and a single rack is shown to be present only on a first analysis unit. That is, it is seen that the sum of racks present on the rack standby disk and on the analysis-side connection lines is nine in number.

The control unit 19 judges that timing, in which racks are supplied from the rack supply section 3 and in which racks are recovered to the rack recovery section 4, and controls transfer of racks so that the number N of the sum of racks does not exceed the number of those racks, which can be held on the rack standby disk 5, that is, the number M of the rack receipt sections. In other words, only when the sum of the number of racks actually held on the rack standby disk and the number of racks present on all the exclusive analysis-side connection lines is less than the number of those racks, which can be held on the rack standby disk, the control unit controls transfer of racks so that fresh racks from the rack supply section 3 are received, by the rack standby disk, in a pretreatment rack receipt position.

In this case, the total number of racks includes the number of particular racks such as racks for quality control (control racks) which are controlled so as not to be recovered toward the rack recovery section 4 from the rack standby disk during the analyzing operation of the automatic analyzer, calibrator racks (racks for correction), cleaning racks and the like. The control unit controls the number of racks in a manner to ensure at least one empty rack position (rack receipt section) so that an emergency rack or racks can be received by the rack standby disk at any time.

Even during treatment of specimens in other racks, an emergency rack charged with a container of a specimen, which needs analytical measurements of urgency, is set to force its way at a forefront of a row of racks on the rack supply section 3. Such emergency rack is transferred to the rack standby disk immediately after specimen ID or rack ID is read by the bar-code reading device 17. On the basis of the read information and an emergency information of an emergency specimen stored beforehand, the control unit 19 has the information storage unit 18 storing the fact that a specimen being an object of analysis and disposed on the emergency rack is currently present on the rack feed line 6, and controls subsequent transfer operation of the emergency rack.

In the case where the sampling and treatment of the above-mentioned common specimen are being implemented in the specimen sampling position A1 of the analysis unit 2 when the emergency rack is received by the rack standby disk 5, the sampling operation of the common specimen is temporarily suspended. That is, the common specimen in the specimen sampling position A1 is returned to the rack standby disk so as to be retreated into an empty rack receipt section on the rack standby disk, and continuously the emergency rack is positioned in the access position T3 for analysis in a corresponding analysis unit. Such positional information is stored in the information storage unit. And the rack moving pawl 23 serving as a rack reciprocating transfer means is used to transfer the emergency rack to the specimen sampling position A1, so that specimen sampling for emergency items of analysis is implemented by the sampling mechanism 26.

The emergency rack, for which the sampling operation of an emergency specimen has been terminated, is returned to the rack standby disk 5 by the rack moving pawl 23. Subsequently, the common rack having been temporarily retreated onto the rack standby disk is positioned in the access position for analysis, and returned, by the rack moving pawl 23, to the specimen sampling position A1 on the analysis-side connection line 22 where any rack is not present, and the specimen sampling operation having remained midway is reopened. In the meantime the emergency rack is carried out toward the rack recovery section 4 from the rack standby disk 5 to be recovered. The common rack, for which the sampling operation has been completed in the specimen sampling position A1, is returned to the rack standby disk 5 and carried out toward the rack recovery section 4 positioned in the carrying-out position T2 in case of no need of further measurements.

The evaporation protecting chamber 60 shown in FIG. 3 is provided with the humidifier 36, which increases the humidity of an air within the protecting chamber relative to the humidity of an outside air to prevent evaporation of various specimens and the cleaning liquid held on various racked on the rack standby disk 5. An example of the evaporation protecting chamber provided with the humidifier is shown in FIG. 6. The evaporation protecting chamber 60 comprises a light-transmitting lid 61 disposed on an upper portion thereof and capable of opening and closing, and a chamber 62 substantially isolated from outside. The rack standby disk 5 is disposed in the chamber 62 to be made rotatable by the drive mechanism 21. The evaporation protecting chamber 60 is connected to rack transfer passages such as the rack feed line 6, the rack recovery line 7, the analysis-side connection line 22 and the like while blocks for restricting inflow and outflow of air are provided at boundaries between the chamber and the rack transfer passages.

An example of such blocks is an opening and closing door operatively controlled to be made open at the time of passage of a rack or racks. In this case, the door is laterally slidable such that it is timed with the passage of a rack or racks to be slid by the drive mechanism. After the passage of a rack or racks, the slide door is closed by the drive mechanism. Another example of such blocks comprises a plurality of flexible, strip-shaped sheets of a synthetic resin aligned at the boundaries. The sheets are fixed only at upper ends thereof and free at lower ends and both side ends. When a rack passes the boundaries, the rack itself can advance pushing aside the sheets, so that the drive mechanism is dispensed with.

The humidifier 36 shown in FIG. 6 comprises a top-opened water containing dish 37, an evaporation assisting material 38 having its lower end immersed in the water in the water containing dish and being porous to have a large surface area, a blasting fan 39, and a water-level sensor 41 for detecting a liquid surface in order to adjust a water level. Water from a water reservoir 63 is supplied to the water containing dish through an electromagnetic valve 42 by a liquid feed pump 64. The operation of the liquid feed pump 64 is controlled in accordance with a detection signal from the water-level sensor 41. The evaporation assisting material 38 is, for example, cloth pieces. These cloth pieces draw up the water from the water reservoir 63 due to the capillary phenomenon, and air fed by the fan 39 flows toward the chamber 62 along surfaces of a plurality of cloth pieces as stretched. Since air is dampened when passing an area where the cloth pieces are stretched, the air, of which humidity is increased, is fed into the chamber 62.

A humidity sensor 40 is arranged in the chamber 62 to monitor humidity in the chamber 62. When the humidity becomes equal to or lower than a preset value, the control unit 19 judges that a detection signal from the humidity sensor 40 is equal to or below a set value, and actuates and controls the fan 39 to feed a high-humidity air toward the chamber 62. Also, when the water level becomes equal to or below a set value, the control unit 19 opens the electromagnetic valve 42 driving the liquid feed pump 64 to feed water to the water containing dish 37. In this manner, a higher humidity than the particular value is maintained in the chamber 62, whereby it is possible to decrease drying of specimens held on the respective racks arranged on the rack standby disk 5 and to preserve the specimens over a long term without change in quality.

Held on the rack standby disk 5 at all times are particular racks charged with containers, which contain therein liquids being repeatedly fed to the analysis unit whenever quality control specimens, calibrators, cleaning liquids and so on are needed. These racks are placed over a long term in the evaporation protecting chamber 60 with caps of the respective containers being removed. However, since a high humidity is maintained in the evaporation protecting chamber 60, evaporation of control specimens and calibrators can be prevented with the result that change in quality is avoided over a long term. Also, temperature control is effected in the evaporation protecting chamber 60 in a manner to keep a lower temperature (a particular temperature in the range of 5 to 10 centigrade degrees) than room temperature, so that it is possible to prevent specimens or the like from being further deteriorated.

The automatic analyzer is shown in FIG. 1 as comprising a minimum unit, in which a single rack delivery unit 1 is combined with a single analysis unit 2. It is easy to install more analysis units in the automatic analyzer shown in FIG. 1. It suffices that analysis-side connection lines exclusively used for the analysis units further installed be arranged to be able to be connected to the rack standby disk 5 and the rack standby disk 5 be operatively controlled to allow the racks to be stopped in access positions for analysis for the additionally installed analysis units.

Figure 9:
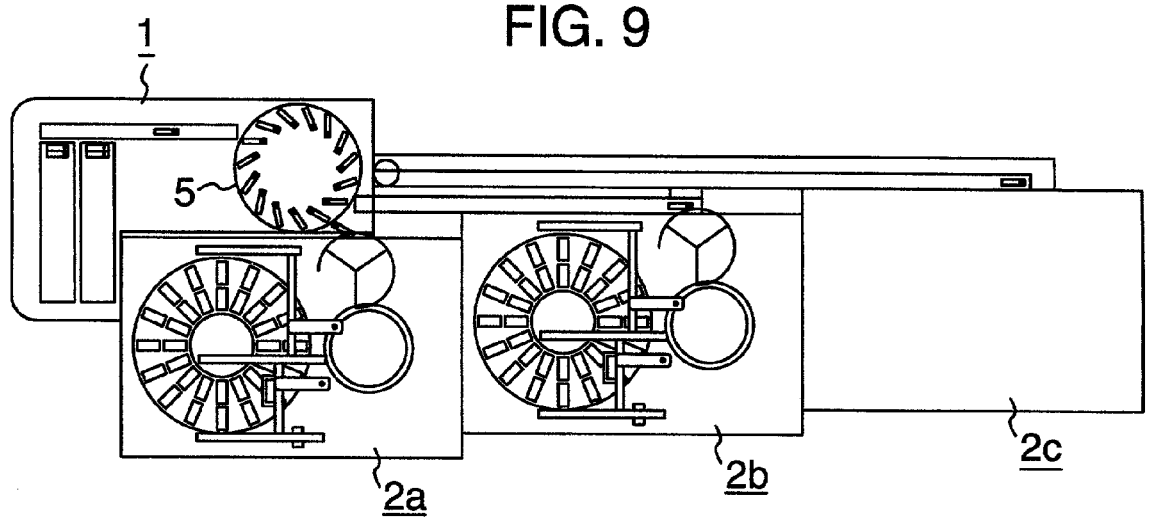
FIG. 9 is a schematic, plan view showing an example of an arrangement, in which three analysis units are combined.
Figure 10:
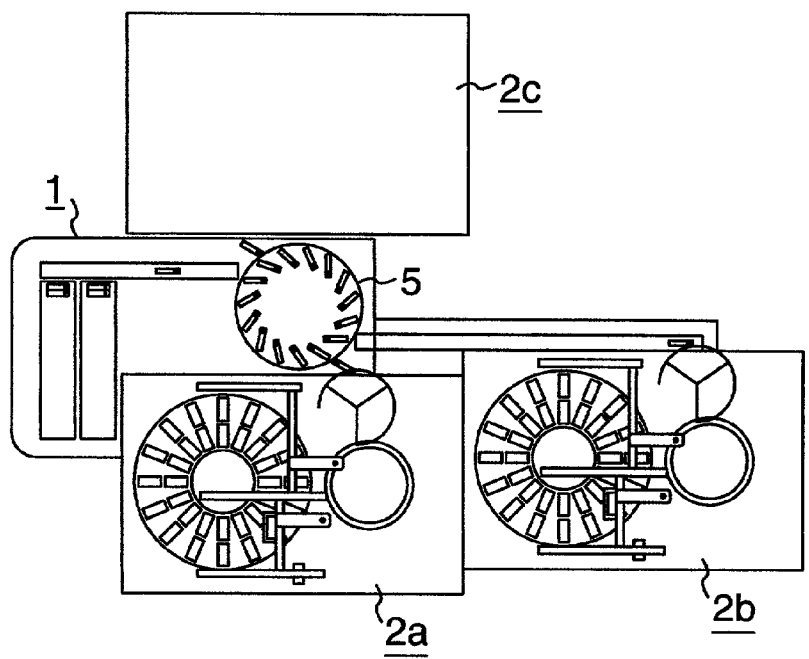
FIG. 10 is a schematic, plan view showing another example of an arrangement, in which three analysis units are combined.

FIGS. 7 and 8 show respective examples, in which two analysis units 2a, 2b are combined with a single rack delivery unit 1, FIGS. 9 and 10 showing respective examples, in which three analysis units 2a, 2b and 2c are combined with a single rack delivery unit 1. In either case, additional analysis units can be installed without any mechanical modification of the rack delivery unit 1.

The exemplary combination shown in FIG. 7 will be explained with reference to FIGS. 7 and 4. The bar-code reading device 17 reads a specimen ID or rack ID of a rack transferred to the rack feed line 6 from the rack supply section 3, the control unit 19 verifies the relationship between respective specimens and analysis items as requested, and analysis information is stored in the information storage unit 18. The control unit 19 judges, on the basis of the analysis information stored in the information storage unit 18, that analysis unit, to which each rack should be transferred, and has the information storage unit 18 storing the results. When that analysis unit, to which an associated rack delivered at the carrying-in position T1 to the rack standby disk 5 from the rack feed line 6 is to be transferred, is the analysis unit 2b disposed far away from the rack standby disk 5, the rack standby disk 5 is rotationally controlled by the control unit 19 in a manner to position the associated rack in an access position T4 for analysis, corresponding to an analysis-side connection line 22b being a reciprocating transfer passage exclusively used for the analysis unit 2b.

The analysis-side connection line 22b serving as a rack transfer mechanism has a rack moving pawl similar to that shown in FIG. 3, so that an associated, single rack is transferred by the rack moving pawl to one end side of the analysis-side connection line 22b and further to a specimen sampling position A2 on the analysis unit 2b. The specimen sampling position A2 is on a side of the other end of the analysis-side connection line 22b. A specimen to be subjected to the analysis and treatment by the analysis unit 2b is caused by a pipette nozzle of a specimen sampling mechanism 26b to be dispensed at the specimen sampling position A2 into a reaction container on a reaction disk 27b from a specimen container on the rack. The aftertreatment rack, for which sampling of a specimen has been completed, is transferred toward the rack standby disk 5 by way of the analysis-side connection line 22b. The aftertreatment rack transferred to an empty rack receipt section 57 on the rack standby disk by the rack moving pawl is positioned in the carrying-out position T2 with the rotating operation of the rack standby disk 5 to be recovered to the rack recovery section 4 via the rack recovery line 7.

In the case where a pretreatment rack received onto the rack standby disk 5 from the rack supply section 3 is to be subjected to analysis and treatment by another analysis unit 2a, the same transferring and treating operation as that explained with reference to FIG. 1 is effected, and so an explanation is omitted for the sake of avoiding duplication. An example shown in FIG. 8 is different from that shown in FIG. 7 only in the arrangement and orientation of the analysis unit 2b but the same as that shown in FIG. 7 with respect to the transferring action of racks, and so any detailed explanation therefor is omitted. In the example shown in FIG. 8, the analysis unit 2b is disposed in rotation symmetry relative to the analysis unit 2a, and so the exclusive analysis-side connection line therefor can be made extremely short.

Since the operation of analysis and treatment is carried out independently in the two analysis units 2a, 2b, many kinds of analysis items as a whole can be efficiently measured. Also, in the case where racks are to be transferred to the two analysis units from the rack standby disk 5, they are transfer-controlled by the control unit 19 such that while one of the analysis units performs sampling and treatment of a preceding rack, a subsequent rack is transferred to the other of the analysis units. Thereby, the capacity of specimen treatment is not decreased in the respective analysis units. Also, since the respective analysis units comprise a reciprocating transfer device for exclusive use between them and the common rack standby disk, the entire analyzing operation can be continued by setting that the other of the analysis units can dispose the same analysis items as those for one of the analysis units even when the reciprocating transfer device on one of the analysis units becomes difficult to transfer a rack or racks due to any possible trouble in terms of transfer and treatment. Thereby, it is possible to avoid a possible damage that the automatic analyzer cannot be used as a whole.

In examples shown in FIGS. 9 and 10, an additional analysis unit 2c is installed on the constitution in the examples shown in FIGS. 7 and 8. The additionally installed analysis unit 2c is also provided with a reciprocating transfer device for exclusive use, and the same rack transfer operation as that described previously is performed. In accordance with an actual floor area usable in an examining equipment where the automatic analyzer is installed, either of the arrangement shown in FIG. 9 and the arrangement shown in FIG. 10 is suitably chosen.

With the arrangement, in which a plurality of analysis units are connected to the rack delivery unit as shown in FIGS. 7 to 10, one or two out of the analysis units can be made analysis unit or units, which employ different methods of analysis. For example, with the automatic analyzer arranged and designed as shown in FIG. 9, biochemical analysis units may be arranged on the analysis units 2a, 2b to perform analysis and treatment with respect to items of biochemical analysis and immunity analysis units may be arranged on the analysis unit 2c to perform analysis and treatment with respect to items of immunity analysis.

With the automatic analyzer, in which biochemical analysis units and immunity analysis units are included, the control unit 19 performs specific handling of racks for both analyses, in which are held specimens being analyzed with respect to both the items of biochemical analysis and the items of immunity analysis. More specifically, when a rack is judged on the basis of information read by the bar-code reading device 17 to be a rack for both analyses and the rack for both analyses is received in the rack standby disk 5 of the rack delivery unit 1, the control unit 19 positions, prior to transferring of the rack for both analyses toward the biochemical analysis units 2a, 2b, the rack for both analyses in the access position T4 for analysis on the immunity analysis unit 2c from the rack standby disk 5, and transfers the rack for both analyses to a specimen sampling position on the immunity analysis unit 2c to first have the same sampling a specimen for the items of immunity analysis. Subsequently, the rack for both analyses having been subjected to the sampling and treatment of a specimen in the immunity analysis unit is returned to the rack standby disk 5 to be positioned in the access position for analysis corresponding to the biochemical analysis unit 2a or 2b to be transferred to the specimen sampling position from the rack standby disk for sampling of a specimen for the items of biochemical analysis. Subsequently, the rack for both analyses is returned to the rack standby disk to be recovered.

The items of immunity analysis are liable to be affected by mutual contamination of specimens as compared with the items of biochemical analysis. However, such control in transfer can decrease that adverse influence, which produces degradation of accuracy on results of analysis with respect to the items of immunity analysis.

With the above-mentioned embodiments, various arrangements and configurations can be chosen in installation of additional analysis units being connected to the rack delivery unit, so that an automatic analyzer can be provided to be capable of flexibly corresponding to the need of an examining equipment installed.

The automatic analyzer, to which the invention is applied, is characteristically related to a method of carrying out a pretreatment rack, which holds a specimen and has not yet been subjected to the sampling and treatment of a specimen, toward the analysis unit from the rack supply section, and transferring an aftertreatment rack, which has been subjected to the sampling and treatment of a specimen by the analysis unit, so as to have the same recovered onto the rack recovery section. Whether a rack being read is a common rack holding a common specimen or a control rack holding a specimen for quality control is judged on the basis of results of reading of discriminating information of a specimen or a rack by the reading device. In this case, control racks, pretreatment racks and aftertreatment racks are held in a mixed state by the rack standby disk capable of holding a plurality of racks. A common rack is transferred to the specimen sampling position on the analysis unit from the rack standby disk, and is carried out toward the rack recovery section from the rack standby disk after it is returned to the rack standby disk after the sampling and treatment of the specimen. However, the control rack is transferred to the specimen sampling position on the analysis unit from the rack standby disk and returned to the rack standby disk after the sampling and treatment of a specimen for quality control, and thereafter is made to stand by on the rack standby disk until a subsequent time of measurement.

Such arrangement enables making the constitution of the transfer system simple and easily managing a special specimen, such as a specimen for quality control, repeatedly used as desired, and a common specimen such as a patient specimen. In a desired embodiment, racks for correction, holding a specimen for correction, and cleaning liquid racks holding a cleaning liquid, as well as racks for quality control are held on the rack standby disk, and the racks for correction and the cleaning liquid racks are made to stand by on the rack standby disk until a subsequent time, at which the analysis unit needs a specimen for correction or a cleaning liquid.

The automatic analyzer has another feature related to an analysis unit which samples a specimen from racks holding specimen containers and analyzes analysis items, of which analysis is indicated with respect to the sampled specimen, a rack delivery unit which supplies to the analysis unit a pretreatment rack prior to sampling of the specimen by the analysis unit and recovers an aftertreatment rack, for which the sampling and treatment of the specimen have been completed, to the analysis unit, and a reading device which reads the discriminating information of a specimen or a rack with respect to the pretreatment rack. The rack standby disk allows control racks holding a specimen for quality control, pretreatment racks and aftertreatment racks to stand by in a mixed state, and operatively rotates these racks to stop the same in a pretreatment rack receipt position where pretreatment racks are received from the rack supply section, an access position to the analysis unit and an aftertreatment rack carrying-out position where aftertreatment racks can be carried out toward the rack recovery section. The reciprocating transfer device is used to transfer racks between the access position to the analysis unit and the specimen sampling position on the analysis unit. The control unit judges, on the basis of results of reading by the reading device, whether a rack being read is a common rack holding a common specimen or a control rack, and controls transfer of racks in a manner to carry out the common rack toward the rack recovery section from the aftertreatment rack carrying-out position when a rack received in the access position is a common rack, and to cause a rack received in the access position to stand by on the rack standby disk until a subsequent time of measurement when the rack is a control rack.

The rack standby disk is arranged in an appropriate manner whereby the automatic analyzer as a whole is made small-sized even when it is of a minimum unit composed of a single analysis unit. Also, such minimum unit can be made use of as it is when analysis units are additionally installed.

In a desired embodiment, the rack standby disk is arranged in the rack delivery unit to become easy to handle. The number of transfer passages is reduced by using the pretreatment rack receipt position and the aftertreatment rack carrying-out position in common. In a particularly desired configuration, the rack standby disk is arranged in the evaporation protecting chamber, in which air is maintained higher in humidity than an outside air. Thereby, even if a common specimen such as a patient specimen is held by the rack standby disk over a long time, it can be prevented from drying, and a special specimen, such as a specimen for quality control, repeatedly used can be prevented from varying in concentration of components due to drying. The evaporation protecting chamber is provided with a humidifier which has a humidity sensor and is operatively controlled in a manner to maintain an interior of the evaporation protecting chamber.

When an emergency rack holding a specimen, which needs urgent measurements, is received by the rack standby disk, a rack, for which the sampling and treatment of a specimen is being performed in the analysis unit, is suspended in the treatment and retreated onto the rack standby disk, and then the emergency rack is transferred to the specimen sampling position on the analysis unit from the rack standby disk and returned to the rack standby disk after the sampling and treatment of a specimen, then the suspended rack is transferred to the specimen sampling position on the analysis unit from the rack standby disk so that the sampling and treatment of a specimen is resumed for the suspended rack.

The automatic analyzer has a further feature related to the provision of a plurality of analysis units. In this case, the rack standby disk is rotatingly actuated to stop in respective access positions of the plurality of analysis units. Reciprocating transfer passages provided exclusively every analysis unit allow racks to move reciprocatingly between those access positions on the rack standby disk, which correspond to the respective analysis units, and specimen sampling positions on the respective analysis units. The control unit controls transfer of racks such that a single rack is reciprocatingly transferred on the respective reciprocating transfer passages for exclusive use, and after a preceding rack is returned to the rack standby disk from a specimen sampling position on the analysis unit, to which the rack has been transferred, a subsequent rack bound for the same analysis unit is transferred via an exclusive reciprocating transfer passage.

Such arrangement enables installation of additional analysis units without modifying of a common transfer system and avoiding large-sizing of the entire automatic analyzer. Also, it is possible to readily choose an analysis unit, to which a rack is to be transferred, and to rapidly present an appropriate rack to a predetermined analysis unit without confusion.

In a desired embodiment, the control unit controls transfer of racks such that so long as the sum of the number of racks actually held on the rack standby disk and the number of racks present on all the reciprocating transfer passages for exclusive use is smaller than the number of racks that can be held on the rack standby disk, a fresh rack from the rack supply section is received in a pretreatment rack receipt position on the rack standby disk. Thereby, it is possible to avoid confusion in the transfer and treatment of racks.

When a plurality of analysis units in the automatic analyzer include biochemical analysis units that perform analysis with respect to items of biochemical analysis and immunity analysis units that perform analysis with respect to items of immunity analysis, the control unit controls transfer of racks in such a manner that when a rack for both analyses, holding a specimen, for which items of biochemical analysis and items of immunity analysis are to be analyzed, is received by the rack standby disk, the rack for both analyses is transferred to an immunity analysis unit from the rack standby disk before being transferred to a biochemical analysis unit, and after the rack for both analyses having been subjected to the sampling and treatment of a specimen in the immunity analysis unit is returned to the rack standby disk, it is transferred to a specimen sampling position on the biochemical analysis unit from the rack standby disk. Thereby, it is possible to keep reliability on results of analysis with respect to items of immunity analysis that are liable to be affected by carry-over of specimens.

Also, the control unit controls transfer of racks in such a manner that until re-measurement is decided on the basis of results of analysis of a specimen sampled at any analysis unit, a rack having been subjected to the sampling and treatment of a specimen is caused to stand by on the rack standby disk, and when re-measurement is necessary, the rack having stood by is again transferred to the specimen sampling position on the analysis unit from the rack standby disk.

The invention claimed is:

1. An automatic analyzer comprising:
   an analysis unit for analyzing specimens;
   a plurality of common racks holding patient specimens to be sampled for analysis by the analysis unit;
   a plurality of specific racks holding specific liquids to be repeatedly sampled as needed for analysis of the patient specimens by the analysis unit;
   a rack supply section that supplies the common racks and the specific racks to be used in analysis by the analysis unit;
   a rack feed line, connected to the rack supply section, that receives the common racks and the specific racks from the rack supply section;
   a rack standby disk, connected to the rack feed line, that receives the common and specific racks from the rack feed line and supplies the common racks and specific racks to the analysis unit;
   a rack transfer means that transfers the common and specific racks from the rack standby disk to a specimen sampling position on the analysis unit and returns the common racks and the specific racks, from which the specimens and specific liquids have been sampled in the specimen sampling position, to the rack standby disk,
   a rack recovery line, connected to the rack standby disk, that receives the common racks having been analyzed by the analysis unit from the rack standby disk;
   a rack recovery section, connected to the rack recovery line, that receives the common racks having been analyzed by the analysis unit from the rack recovery line;
   a control unit connected to the rack supply section, the rack feed line, the rack standby disk and the rack recovery line controlling transfer of the common racks and the specific racks from the rack supply section to the rack standby disk, controlling rotating and stopping of the rack standby disk in a state such that the common racks and the specific racks are made to stand by thereon in a mixed state, and controlling transferring of the common racks on the rack standby disk towards the rack recovery section after treatment;

a reading device which reads discriminating information of the common and the specific racks prior to the rack standby disk receiving the common and specific racks from the rack feed line, and disposed proximate to the rack feed line;

wherein said control unit controls transfer of the common racks and specific racks based on the discriminating information read by the reading device such that the common racks are carried toward the rack recovery section after having been analyzed by the analysis unit, and the specific racks are kept standing by on the rack standby disk.

2. The automatic analyzer according to claim 1, wherein said rack standby disk is disposed in a rack delivery unit.

3. The automatic analyzer according to claim 1, wherein a position of the rack standby disk for receipt of a pretreatment rack from the rack feed line in which a specimen is to be sampled and a position of the rack standby disk for carrying-out of an aftertreatment rack from which a specimen has been sampled are used in common.

4. The automatic analyzer according to claim 1, wherein said rack standby disk is disposed in an evaporation protecting chamber, in which air is maintained higher in humidity than an outside air.

5. The automatic analyzer according to claim 4, wherein said evaporation protecting chamber is provided with a humidifier having a humidity sensor, which is operatively controlled to maintain an interior of the evaporation protecting chamber at a predetermined humidity or higher.

6. The automatic analyzer according to claim 1, wherein said rack feed line is further for transferring an emergency rack holding a patient specimen to be analyzed and the control unit controls transfer of the emergency rack to be received by said rack standby disk, and, when said rack standby disk holds the emergency rack, another one of the racks for which sampling and treatment of a specimen is being performed in said analysis unit, is suspended and temporarily returned onto the rack standby disk, wherein the emergency rack is transferred to the specimen sampling position on the analysis unit from the rack standby disk and returned to the rack standby disk after the sampling and treatment of the specimen, and wherein the suspended rack is then transferred to the specimen sampling position on the analysis unit from the rack standby disk so that the sampling and treatment of the specimen are resumed for the suspended rack.

7. An automatic analyzer comprising:
an analysis unit for analyzing specimens;
a plurality of common racks holding patient specimens to be sampled for analysis by the analysis unit;
a plurality of specific racks holding specific liquids to be repeatedly sampled as needed for analysis of the patient specimens by the analysis unit;
a rack supply section that supplies the common racks and the specific racks to be used in analysis by the analysis unit;
a rack feed line, connected to the rack supply section, that transfers the common racks and the specific racks from the rack supply section;
a rack standby disk, connected to the rack feed line, that receives the common racks and the specific racks from the rack feed line, rotating and stopping in a state such that the common racks and specific racks are made to stand by thereon in a mixed state;
a rack recovery line that receives the common racks from the rack standby disk;
a rack recovery section that receives the common racks from the rack recovery line;
a reading device which reads discriminating information of the common racks and the specific racks prior to the rack standby disk receiving the common racks and the specific racks from the rack feed line, and disposed proximate to the rack feed line;
a rack transfer means which operates to transfer the common racks and the specific racks from the rack standby disk to a specimen sampling position on an analysis unit and to return the common racks and the specific racks, from which the specimens and specific liquids have been sampled in specimen sampling position, to the rack standby disk; and
a control unit controlling transfer of the common racks and the specific racks based on the discriminating information read by the reading device and after one of either the common racks or specific racks is returned to the rack standby disk from the specimen sampling position, another one of either the common racks or specific racks is transferred to the sampling position via the rack transfer means.

8. The automatic analyzer according to claim 7, wherein the rack transfer means has at least one transfer passage, and wherein said control unit controls transfer of the racks in a manner that so long as the sum of the number of racks actually held on the rack standby disk and the number of racks present on the at least one transfer passage of the rack transfer means is smaller than the number of racks that can be held on the rack standby disk, either another common rack or specific rack from the rack supply section is received on the rack standby disk.

9. The automatic analyzer according to claim 7, wherein said analysis unit is one among multiple units including biochemical analysis units which analyze items of biochemical analysis and immunity analysis units which analyze items of immunity analysis, and said control unit controls transfer of the racks in a manner that when one of the common racks holding a specimen, for which items of biochemical analysis and items of immunity analysis are to be analyzed, is received on the rack standby disk, the one of the common racks is transferred to the immunity analysis unit from the rack standby disk before being transferred to the biochemical analysis unit, and after the one of the common racks having been subjected to sampling and treatment of the specimen in the immunity analysis unit is returned to the rack standby disk, the one of the common racks is transferred to a specimen sampling position on the biochemical analysis unit from the rack standby disk.

10. The automatic analyzer according to claim 7, wherein said control unit controls transfer of the racks in a manner that until re-measurement is decided on the basis of results of analysis of a specimen sampled at the analysis unit, one of the common racks having been subjected to sampling and treatment of the specimen is kept standing by on the rack standby disk, and when re-measurement is necessary, the one of the common racks having stood by is again transferred to the specimen sampling position on the analysis unit from the rack standby disk.

* * * * *